United States Patent
Tang et al.

(10) Patent No.: US 11,072,575 B1
(45) Date of Patent: Jul. 27, 2021

(54) METHOD OF PREPARING A CINNAMYL ALCOHOL RETINOIC ACID ESTER WITH ANTIOXIDANT AND ANTIBACTERIAL ACTIVITIES

(71) Applicants: Yonghong Tang, Xi'an (CN); Minghui Chang, Xi'an (CN); Huafeng Qi, Xi'an (CN); Peiyu Zhou, Xi'an (CN); Zhuanmei Yuan, Xi'an (CN); Wenbo Yao, Xi'an (CN); Guaiping Qiao, Xi'an (CN); Bin Tian, Xi'an (CN); Juan Li, Xi'an (CN)

(72) Inventors: Yonghong Tang, Xi'an (CN); Minghui Chang, Xi'an (CN); Huafeng Qi, Xi'an (CN); Peiyu Zhou, Xi'an (CN); Zhuanmei Yuan, Xi'an (CN); Wenbo Yao, Xi'an (CN); Guaiping Qiao, Xi'an (CN); Bin Tian, Xi'an (CN); Juan Li, Xi'an (CN)

(73) Assignee: XI'AN TAIKOMED PHARMACEUTICAL TECHNOLOGY CO., LTD., Xi'an (CN)

(*) Notice: Subject to any disclaimer, the term of this patent is extended or adjusted under 35 U.S.C. 154(b) by 0 days.

(21) Appl. No.: 17/026,221

(22) Filed: Sep. 19, 2020

(51) Int. Cl.
*C07C 67/08* (2006.01)
*A01N 37/10* (2006.01)
*C07C 67/56* (2006.01)
*C07C 69/608* (2006.01)

(52) U.S. Cl.
CPC ............ *C07C 67/08* (2013.01); *A01N 37/10* (2013.01); *C07C 67/56* (2013.01); *C07C 69/608* (2013.01)

(58) Field of Classification Search
CPC ..... C07C 67/08; C07C 69/608; C07C 69/612; A01N 37/10
See application file for complete search history.

(56) References Cited

U.S. PATENT DOCUMENTS

| | | | | |
|---|---|---|---|---|
| 5,045,533 A | * | 9/1991 | Philippe | A61K 8/671 514/29 |
| 5,696,276 A | * | 12/1997 | Ahn | C07C 46/02 552/298 |
| 2018/0290973 A1 | * | 10/2018 | Babrou | C07C 403/20 |

* cited by examiner

*Primary Examiner* — Yate' K Cutliff

(57) ABSTRACT

A method of preparing a compound of formula (I):

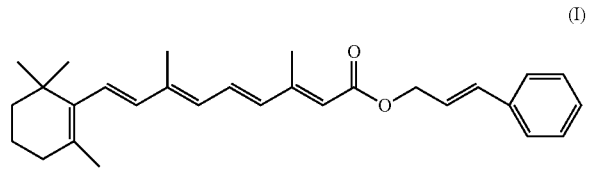

(I)

is disclosed. The compound of formula (I) can be used as an antioxidant agent. The compound can also be used as an antibacterial agent to inhibit *Staphylococcus aureus* 18-596 and *Staphylococcus aureus* 18-596.

16 Claims, 3 Drawing Sheets

METHOD OF PREPARING A CINNAMYL ALCOHOL RETINOIC ACID ESTER WITH ANTIOXIDANT AND ANTIBACTERIAL ACTIVITIES

FIELD OF THE INVENTION

The present invention relates to the field of medicinal chemistry, and in particular, to a method of preparing a cinnamyl alcohol retinoic acid ester with antioxidant and antibacterial activities.

BACKGROUND OF THE INVENTION

With the widespread use of antibiotics, drug-resistant strains have become more common pathogens that cause clinical infections. At present, the most common drug-resistant gram-positive bacteria in the clinic are methicillin-resistant *Staphylococcus* (MRSA), penicillin-resistant pneumococcus (PRSP), and vancomycin-resistant *enterococcus* (VRE). Infection of drug-resistant strains in hospitals has greatly increased the mortality rate, and its treatment has become a clinical problem. The development of effective drugs is imminent.

The natural product of cinnamyl alcohol (compound of formula II) is present in Peru balsam, cinnamon leaf, hyacinth oil and sesame balsam in the form of esters. It is commonly used as a fixative and modifier. It is also an important raw material for medicine, usually used to synthesize cardiovascular and cerebrovascular drugs. It is used clinically to treat various tumors, such as uterine cancer, ovarian cancer and esophageal cancer.

Retinoic acid (compound of formula III) is a commonly used drug in dermatology. It is a metabolic intermediate product of vitamin A in the body. It has a certain therapeutic effect on many diseases with complete keratosis, incomplete keratosis, and hyperkeratosis. In addition, it also has anti-tumor, wound healing and anti-infection effects.

In the present invention, the cinnamyl alcohol is modified by the retinoic acid structure to obtain a novel cinnamyl alcohol retinoic acid ester. Preliminary antibacterial activity experiment shows that the compound has excellent antibacterial activity and has high medical research and application value in the treatment of infectious diseases caused by multidrug resistant bacteria.

SUMMARY OF THE INVENTION

In one embodiment, the present invention provides a cinnamyl alcohol retinoic acid ester which can be used as an excellent anti-oxidation and preparation of scavenging free radical products in the fields of food, health care products and medicine. The structural formula of the compound of the present invention is as shown in Formula I:

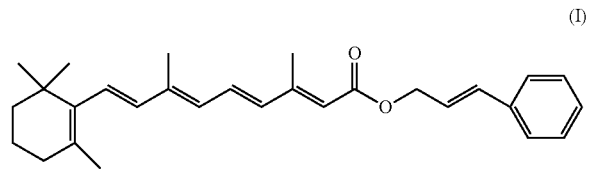 [SMILES: CC1=C(/C=C/C(C)=C/C=C/C(C)=C/C(=O)OC/C=C/c2ccccc2)C(C)(C)CCC1]

(I)

In another embodiment, the present invention provides a method of reacting a compound of formula (II) with a compound of formula (III) in an organic solvent to obtain the compound of formula (I), preparing a composition that includes the compound of formula (I), and applying the composition as antioxidant agent.

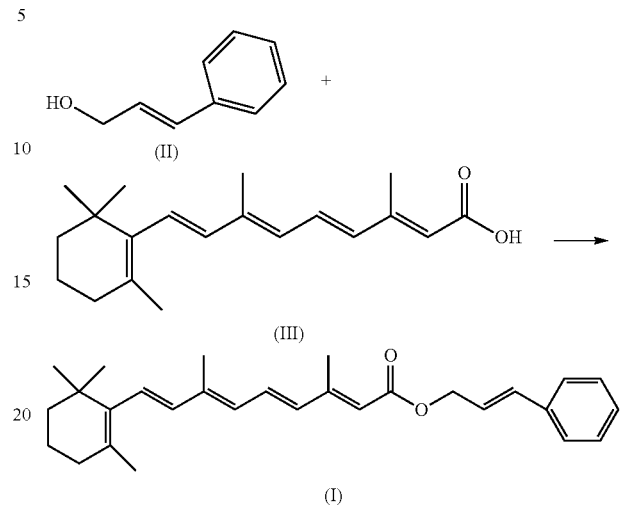

In another embodiment, the method further includes applying the composition as antibacterial agent to inhibit *Staphylococcus aureus* 18-596 and *Staphylococcus aureus* 18-596.

In another embodiment, the reaction of the compound of formula (II) with the compound of formula (III) includes the following steps: placing the compound of formula (II) and the compound of formula (III), in a molar ratio of 1:1 to 1:1.3, in a reactor; adding an organic solvent and a catalytic amount of EDC to obtain a reaction mixture; and heating the reaction mixture at 60-90° C. for 4-8 hours; and purifying the crude product on a silica gel fresh chromatography column with petroleum ether and ethyl acetate as an eluent to obtain the compound of formula (I).

In another embodiment, the organic solvent is toluene, tetrahydrofuran or acetonitrile.

In another embodiment, the organic solvent is toluene.

In another embodiment, the molar ratio of the compound of formula (II) and the compound of formula (III) is 1:1.1.

In another embodiment, the reaction mixture is heated at 80° C.

In another embodiment, the reaction mixture is heated for 7 hours.

In another embodiment, the eluent is petroleum ether:ethyl acetate=1:3.

In another embodiment, the reaction of the compound of formula (II) with the compound of formula (III) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 20-50° C. for 5-10 hours; placing the reaction mixture in a separating funnel to separate a crude product; purifying the crude product by recrystallization in methanol to obtain the compound of formula (I); and recycling the ionic liquid.

In another embodiment, the ionic liquid is 1-methyl-3-n-octylimidazolium tetrafluoroborate, 1-methyl-3-n-octylimidazolium hexafluorophosphate or 1-butyl-3-methylimidazolium tetrafluoroborate ([BMIM][BF4]).

In another embodiment, the ionic liquid is 1-butyl-3-methylimidazolium tetrafluoroborate ([BMIM][BF4]).

In another embodiment, the molar ratio of the compound of formula (II) and the compound of formula (III) is 1:1.1.

In another embodiment, the reaction mixture is heated at 20° C.

In another embodiment, the reaction mixture is heated for 8 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
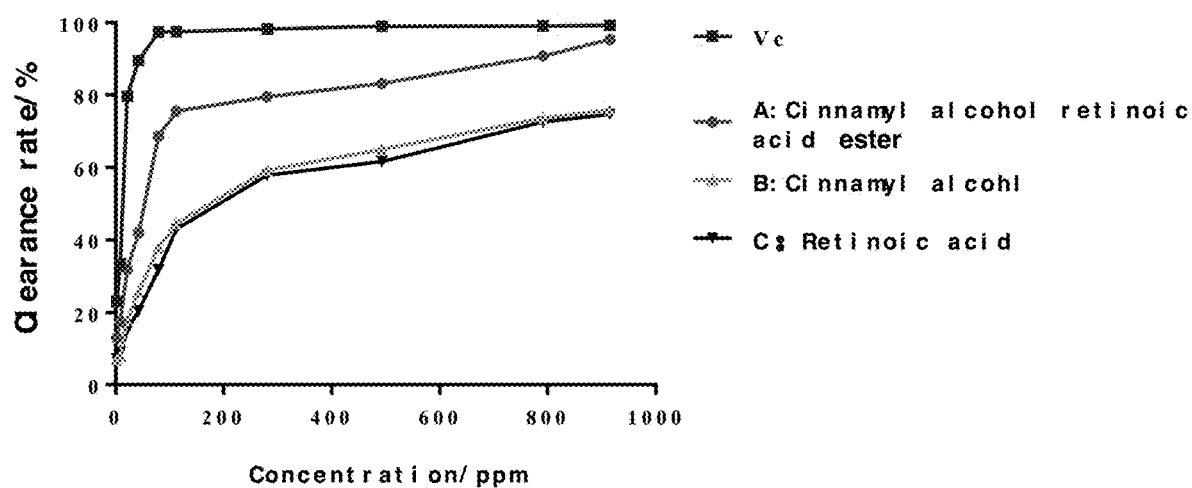
FIG. 1 shows the scavenging rate of the sample and control solution on DPPH free radicals.

Reference will now be made in detail to embodiments of the present invention, example of which is illustrated in the accompanying drawings. The following examples illustrate the present invention, but the present invention is not limited to the following examples.

Example 1

Preparation of Compound (2E,4E,6E,8E)-cinnamyl 3,7-dimethyl-9-(2,6,6-trimethylcyclohex-1-en-1-yl) nona-2,4,6,8-tetraenoate (Compound of Formula I)

In a 250 mL three-necked flask, 67.0 mg (0.50 mmol) of cinnamyl alcohol and 95.7 mg (0.50 mmol) EDC (1-ethyl-3-(3 dimethylaminopropyl)carbodiimide) were dissolved in 60 mL of toluene under nitrogen atmosphere. 165.1 mg (0.55 mmol) of retinoic acid was dissolved in 60 mL of toluene, and slowly added dropwise to the reaction liquid by a separatory funnel. After the completion of the dropwise addition, the temperature was raised to 80° C., and the reaction was carried out for 7 hours. Thin layer chromatography was used to track the reaction to completion, heating was stopped, and the protective device was removed. The reaction mixture was concentrated, washed with water, extracted with ethyl acetate, dried and concentrated to obtain a crude cinnamyl alcohol retinoic acid ester. The crude product was further purified by silica gel column chromatography, eluting with petroleum ether:ethyl acetate=1:3 as eluent, and the eluent was concentrated under reduced pressure and dried to obtain 128.2 mg of the title compound, a total yield of 61.58%.

$^1$H-NMR (400 MHz, DMSO-$d_6$) δ (ppm): 7.45 (2H, d), 7.33 (1H, d), 7.24 (1H, d), 7.05 (1H, d), 6.60 (1H, s), 6.40 (4H, s) 6.23 (2H, s), 5.80 (1H, s), 4.15 (2H, s), 2.30 (2H, t), 2.04 (6H, s), 1.71 (3H, s), 1.61 (2H, t), 1.47 (2H, t), 1.04 (6H, s); $^{13}$C-NMR (400 MHz, DMSO-$d_6$) δ ppm): 168.2, 152.0, 139.4, 137.4, 135.9, 129.0, 126.6, 119.9, 61.9, 40.7, 34.3, 29.3, 19.2, 13.9, 13.1.

Example 2

Preparation of Compound (2E,4E,6E,8E)-cinnamyl 3,7-dimethyl-9-(2,6,6-trimethylcyclohex-1-en-1-yl) nona-2,4,6,8-tetraenoate In a 250 mL three-necked flask, 67.0 mg (0.50 mmol) of cinnamyl alcohol and 95.7 mg (0.50 mmol) EDC were dissolved in 60 mL of acetonitrile under nitrogen atmosphere. 165.1 mg (0.55 mmol) of retinoic acid was dissolved in 60 mL of acetonitrile, and slowly added dropwise to the reaction liquid by a separatory funnel. After the completion of the dropwise addition, the temperature was raised to 90° C., and the reaction was carried out for 4 hours. Thin layer chromatography was used to track the reaction to completion, heating was stopped, and the protective device was removed. The reaction mixture was concentrated, washed with water, extracted with ethyl acetate, dried and concentrated to obtain a crude cinnamyl alcohol retinoic acid ester. The crude product was further purified by silica gel column chromatography, eluting with petroleum ether:ethyl acetate=1:3 as eluent, and the eluent was concentrated under reduced pressure and dried to obtain 115.2 mg of the title compound, a total yield of 55.36%.

Example 3

Preparation of Compound (2E,4E,6E,8E)-cinnamyl 3,7-dimethyl-9-(2,6,6-trimethylcyclohex-1-en-1-yl) nona-2,4,6,8-tetraenoate In a 250 mL three-necked flask, 67.0 mg (0.50 mmol) of cinnamyl alcohol and 95.7 mg (0.50 mmol) EDC were dissolved in 60 mL of tetrahydrofuran under nitrogen atmosphere. 180.1 mg (0.60 mmol) of retinoic acid was dissolved in 60 mL of tetrahydrofuran, and slowly added dropwise to the reaction liquid by a separatory funnel. After the completion of the dropwise addition, the temperature was raised to 60° C., and the reaction was carried out for 8 hours. Thin layer chromatography was used to track the reaction to completion, heating was stopped, and the protective device was removed. The reaction mixture was concentrated, washed with water, extracted with ethyl acetate, dried and concentrated to obtain a crude cinnamyl alcohol retinoic acid ester. The crude product was further purified by silica gel column chromatography, eluting with petroleum ether:ethyl acetate=1:3 as eluent, and the eluent was concentrated under reduced pressure and dried to obtain 121.4 mg of the title compound, a total yield of 58.32%.

Example 4

Preparation of Compound (2E,4E,6E,8E)-cinnamyl 3,7-dimethyl-9-(2,6,6-trimethylcyclohex-1-en-1-yl) nona-2,4,6,8-tetraenoate In a 250 mL three-necked flask, 67.0 mg (0.50 mmol) of cinnamyl alcohol and 95.7 mg (0.50 mmol) EDC were dissolved in 60 mL of toluene under nitrogen atmosphere. 165.1 mg (0.55 mmol) of retinoic acid was dissolved in 60 mL of toluene, and slowly added dropwise to the reaction liquid by a separatory funnel. After the completion of the dropwise addition, the temperature was raised to 70° C., and the reaction was carried out for 4 hours. Thin layer chromatography was used to track the reaction to completion, heating was stopped, and the protective device was removed. The reaction mixture was concentrated, washed with water, extracted with ethyl acetate, dried and concentrated to obtain a crude cinnamyl alcohol retinoic acid ester. The crude product was further purified by silica gel column chromatography, eluting with petroleum ether:ethyl acetate=1:3 as eluent, and the eluent was concentrated under reduced pressure and dried to obtain 115.4 mg of the title compound, a total yield of 55.46%.

Example 5

Preparation of Compound (2E,4E,6E,8E)-cinnamyl 3,7-dimethyl-9-(2,6,6-trimethylcyclohex-1-en-1-yl) nona-2,4,6,8-tetraenoate In a 250 mL three-necked flask, 67.0 mg (0.50 mmol) of cinnamyl alcohol and 95.7 mg (0.50 mmol) EDC were dissolved in 60 mL of acetonitrile under nitrogen atmosphere. 165.1 mg (0.55 mmol) of retinoic acid was dissolved in 60 mL of acetonitrile, and slowly added dropwise to the reaction liquid by a separatory funnel. After the completion of the dropwise addition, the temperature was raised to 75° C., and the reaction was carried out for 7 hours. Thin layer chromatography was used to track the reaction to completion, heating was stopped, and the protective device was removed. The reaction mixture was concentrated, washed with water, extracted with ethyl acetate, dried and concentrated to obtain a crude cinnamyl alcohol retinoic acid ester. The crude product was further purified by silica gel column chromatography, eluting with petroleum ether:ethyl acetate=1:3 as eluent, and the eluent was concentrated under reduced pressure and dried to obtain 119.3 mg of the title compound, a total yield of 57.34%.

Example 6

Preparation of Compound (2E,4E,6E,8E)-cinnamyl 3,7-dimethyl-9-(2,6,6-trimethylcyclohex-1-en-1-yl) nona-2,4,6,8-tetraenoate In a 250 mL three-necked flask, 67.0 mg (0.50 mmol) of cinnamyl alcohol and 95.7 mg (0.50 mmol) EDC were dissolved in 60 mL of tetrahydrofuran under nitrogen atmosphere. 165.1 mg (0.55 mmol) of retinoic acid was dissolved in 60 mL of tetrahydrofuran, and slowly added dropwise to the reaction liquid by a separatory funnel. After the completion of the dropwise addition, the temperature was raised to 65° C., and the reaction was carried out for 8 hours. Thin layer chromatography was used to track the reaction to completion, heating was stopped, and the protective device was removed. The reaction mixture was concentrated, washed with water, extracted with ethyl acetate, dried and concentrated to obtain a crude cinnamyl alcohol retinoic acid ester. The crude product was further purified by silica gel column chromatography, eluting with petroleum ether: ethyl acetate=1:3 as eluent, and the eluent was concentrated under reduced pressure and dried to obtain 121.3 mg of the title compound, a total yield of 58.29%.

Example 7

Preparation of Compound (2E,4E,6E,8E)-cinnamyl 3,7-dimethyl-9-(2,6,6-trimethylcyclohex-1-en-1-yl) nona-2,4,6,8-tetraenoate In a 250 mL three-necked flask, 67.0 mg (0.50 mmol) of cinnamyl alcohol, 165.1 mg (0.55 mmol) of retinoic acid and 8.3 mg (0.005 mmol) silicomolybdic acid were dissolved in 100 mL of 1-butyl-3-methylimidazolium tetrafluoroborate under nitrogen atmosphere. After full dissolution, the reaction was carried out at room temperature (20° C.) for 8 hours. Thin layer chromatography was used to track the reaction to completion, heating was stopped, and the protective device was removed. The reaction mixture system was allowed to separate into layers to give a crude product. The crude product was recrystallized with 70 mL methanol and dried to obtain 177.2 mg of the title compound, a total yield of 85.12%.

Example 8

Preparation of Compound (2E,4E,6E,8E)-cinnamyl 3,7-dimethyl-9-(2,6,6-trimethylcyclohex-1-en-1-yl) nona-2,4,6,8-tetraenoate In a 250 mL three-necked flask, 67.0 mg (0.50 mmol) of cinnamyl alcohol, 165.1 mg (0.55 mmol) of retinoic acid and 8.3 mg (0.005 mmol) silicomolybdic acid were dissolved in 100 mL of 1-butyl-3-methylimidazolium tetrafluoroborate under nitrogen atmosphere. After full dissolution, the reaction was carried out at 50° C. for 5 hours. Thin layer chromatography was used to track the reaction to completion, heating was stopped, and the protective device was removed. The reaction mixture system was allowed to separate into layers to give a crude product. The crude product was recrystallized with 70 mL methanol and dried to obtain 167.3 mg of the title compound, a total yield of 80.39%.

Example 9

Preparation of Compound (2E,4E,6E,8E)-cinnamyl 3,7-dimethyl-9-(2,6,6-trimethylcyclohex-1-en-1-yl) nona-2,4,6,8-tetraenoate In a 250 mL three-necked flask, 67.0 mg (0.50 mmol) of cinnamyl alcohol, 165.1 mg (0.55 mmol) of retinoic acid and 8.3 mg (0.005 mmol) silicomolybdic acid were dissolved in 100 mL of 1-methyl-3-n-octylimidazolium tetrafluoroborate under nitrogen atmosphere. After full dissolution, the reaction was carried out at room temperature (20° C.) for 8 hours. Thin layer chromatography was used to track the reaction to completion, heating was stopped, and the protective device was removed. The reaction mixture system was allowed to separate into layers to give a crude product. The crude product was recrystallized with 70 mL methanol and dried to obtain 167.6 mg of the title compound, a total yield of 80.51%.

Example 10

Preparation of Compound (2E,4E,6E,8E)-cinnamyl 3,7-dimethyl-9-(2,6,6-trimethylcyclohex-1-en-1-yl) nona-2,4,6,8-tetraenoate In a 250 mL three-necked flask, 67.0 mg (0.50 mmol) of cinnamyl alcohol, 165.1 mg (0.55 mmol) of retinoic acid and 8.3 mg (0.005 mmol) silicomolybdic acid were dissolved in 100 mL of 1-methyl-3-n-octylimidazolium tetrafluoroborate under nitrogen atmosphere. After full dissolution, the reaction was carried out at 50° C. for 5 hours. Thin layer chromatography was used to track the reaction to completion, heating was stopped, and the protective device was removed. The reaction mixture system was allowed to separate into layers to give a crude product. The crude product was recrystallized with 70 mL methanol and dried to obtain 164.3 mg of the title compound, a total yield of 78.95%.

Example 11

Preparation of Compound (2E,4E,6E,8E)-cinnamyl 3,7-dimethyl-9-(2,6,6-trimethylcyclohex-1-en-1-yl) nona-2,4,6,8-tetraenoate In a 250 mL three-necked flask, 67.0 mg (0.50 mmol) of cinnamyl alcohol, 165.1 mg (0.55 mmol) of retinoic acid and 8.3 mg (0.005 mmol) silicomolybdic acid were dissolved in 100 mL of 1-methyl-3-n-octylimidazolium hexafluorophosphate under nitrogen atmosphere. After full dissolution, the reaction was carried out at room temperature (20° C.) for 8 hours. Thin layer chromatography was used to track the reaction to completion, heating was stopped, and the protective device was removed. The reaction mixture system was allowed to separate into layers to give a crude product. The crude product was recrystallized with 70 mL methanol and dried to obtain 169.2 mg of the title compound, a total yield of 81.28%.

Example 12

Preparation of Compound (2E,4E,6E,8E)-cinnamyl 3,7-dimethyl-9-(2,6,6-trimethylcyclohex-1-en-1-yl) nona-2,4,6,8-tetraenoate In a 250 mL three-necked flask, 67.0 mg (0.50 mmol) of cinnamyl alcohol, 165.1 mg (0.55 mmol) of retinoic acid and 8.3 mg (0.005 mmol) silicomolybdic acid were dissolved in 100 mL of 1-methyl-3-n-octylimidazolium hexafluorophosphate under nitrogen atmosphere. After full dissolution, the reaction was carried out at 50° C. for 5 hours. Thin layer chromatography was used to track the reaction to completion, heating was stopped, and the protective device was removed. The reaction mixture system was allowed to separate into layers to give a crude product. The crude product was recrystallized with 70 mL methanol and dried to obtain 163.1 mg of the title compound, a total yield of 78.36%.

Example 13

The antioxidant activity of the cinnamyl alcohol retinoic acid ester was measured by a DPPH radical scavenging activity assay.

2,2-Diphenyl-1-picryl hydrazyl (DPPH) is an organic compound composed of a stable organic radical. In the DPPH molecule, due to the presence of multiple electron-withdrawing —$NO_2$ and large π bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Preparation of DPPH Solution:

measuring exact amount of 2,2-diphenyl-1-picryl hydrazyl (DPPH) and dissolving in toluene to prepare a 0.2 mmoL/L DPPH solution, stored at 0° C. in dark.

Preparation of Test Solution:

Vc (positive control), cinnamyl alcohol retinoic acid ester (sample), cinnamyl alcohol (control) and retinoic acid (control). The sample solution was subjected to gradient dilution with toluene, and three sets of controls were separately dissolved in a test tube with a certain amount of toluene to prepare the same concentration gradient as the sample. The corresponding three groups of control solutions were obtained (gradient settings are shown in Table 1).

TABLE 1

| | Dilution gradient of the test solution | |
|---|---|---|
| Number | Test solution | Concentration gradient/ppm |
| Vc | Vc | 1.76, 8.80, 21.12, 42.24, 79.20, 112.64, 281.60, 492.80, 792.00, 915.20 |
| A | Cinnamyl alcohol retinoic acid ester | 1.76, 8.80, 21.12, 42.24, 79.20, 112.64, 281.60, 492.80, 792.00, 915.20 |
| B | Cinnamyl alcohol | 1.76, 8.80, 21.12, 42.24, 79.20, 112.64, 281.60, 492.80, 792.00, 915.20 |
| C | Retinoic acid | 1.76, 8.80, 21.12, 42.24, 79.20, 112.64, 281.60, 492.80, 792.00, 915.20 |

Specific Steps:

Sample liquid absorbance measurement: taking 2 mL of sample solution (Table 1 Vc, B, C), adding 2 mL of DPPH solution with concentration of $2 \times 10^{-4}$ moL/L, mixing and reacting in the dark at room temperature for 30 min, adjusting to zero with toluene, and measuring at 517 nm. The absorbance Ai was simultaneously measured for the absorbance Aj of 2 mL of toluene mixed with 2 mL of the sample solution and the absorbance Ao of 2 mL of DPPH solution mixed with 2 mL of toluene (The experimental results are shown in Table 2).

TABLE 2

| Absorbance test results of each test solution | | | | | | | | | | | |
|---|---|---|---|---|---|---|---|---|---|---|---|
| | | Concentration/ppm | | | | | | | | | |
| Sample | Absorbance | 1.76 | 8.80 | 21.12 | 42.24 | 79.20 | 112.64 | 281.60 | 492.80 | 792.00 | 915.20 |
| Vc | Ai | 0.718 | 0.624 | 0.222 | 0.142 | 0.091 | 0.078 | 0.076 | 0.070 | 0.074 | 0.065 |
| | Aj | 0.068 | 0.061 | 0.050 | 0.054 | 0.069 | 0.057 | 0.062 | 0.062 | 0.066 | 0.059 |
| | Ao | | | | | | 0.846 | | | | |
| A | Ai | 0.826 | 0.788 | 0.653 | 0.567 | 0.333 | 0.279 | 0.336 | 0.204 | 0.138 | 0.087 |
| | Aj | 0.049 | 0.050 | 0.044 | 0.049 | 0.052 | 0.059 | 0.047 | 0.053 | 0.055 | 0.046 |
| | Ao | | | | | | 0.895 | | | | |
| B | Ai | 0.881 | 0.870 | 0.773 | 0.709 | 0.614 | 0.550 | 0.409 | 0.360 | 0.270 | 0.255 |
| | Aj | 0.049 | 0.048 | 0.039 | 0.045 | 0.059 | 0.054 | 0.045 | 0.047 | 0.034 | 0.039 |
| | Ao | | | | | | 0.894 | | | | |

TABLE 2-continued

Absorbance test results of each test solution

| Sample | Absorbance | Concentration/ppm | | | | | | | | |
|---|---|---|---|---|---|---|---|---|---|---|
| | | 1.76 | 8.80 | 21.12 | 42.24 | 79.20 | 112.64 | 281.60 | 492.80 | 792.00 | 915.20 |
| C | Ai | 0.865 | 0.843 | 0.795 | 0.741 | 0.646 | 0.548 | 0.417 | 0.381 | 0.279 | 0.265 |
| | Aj | 0.052 | 0.047 | 0.053 | 0.046 | 0.050 | 0.049 | 0.048 | 0.045 | 0.039 | 0.043 |
| | Ao | | | | | | 0.875 | | | | |

Clearance calculation:

Clearance Rate (%)=[1−(Ai−Aj)/Ao]*100%

TABLE 3

DPPH clearance rate experiment results

| Concentration/ppm | Clearance rate/% ( n = 3) | | | |
|---|---|---|---|---|
| | Vc | A | B | C |
| 1.76 | 23.16 | 13.16 | 6.89 | 7.05 |
| 8.80 | 33.47 | 17.53 | 7.95 | 8.99 |
| 21.12 | 79.63 | 31.95 | 17.86 | 15.23 |
| 42.24 | 89.55 | 42.08 | 25.71 | 20.54 |
| 79.20 | 97.42 | 68.62 | 37.96 | 31.87 |
| 112.64 | 97.53 | 75.46 | 44.56 | 42.96 |
| 281.60 | 98.29 | 79.44 | 59.23 | 57.84 |
| 492.80 | 99.06 | 83.15 | 64.94 | 61.59 |
| 792.00 | 99.10 | 90.77 | 73.54 | 72.52 |
| 915.20 | 99.28 | 95.43 | 75.82 | 74.61 |

Example 14

Antibacterial activity test of the cinnamyl alcohol retinoic acid ester was determined by a paper diffusion drug sensitivity test.

Experimental strains: *Staphylococcus aureus* (SAU) 18-202, multi-resistant *Staphylococcus aureus* 18-596. The experimental strain was identified by Huashan Hospital Affiliated to Fudan University (Institute of Antibiotic of Fudan University).

Drug sensitive paper: The drug sensitive paper is a special drug sensitive paper with a diameter of 6.35 mm and a water absorption of 0.02 mL. The control drug was cefazolin (30 µg/tablet); the test drugs were retinoic acid (30 µg/tablet), cinnamyl alcohol (30 µg/tablet) and cinnamyl alcohol retinoic acid ester (30 µg/tablet).

Reagents: LB agar medium, LA broth medium, 0.5% DMSO solution.

Equipment: Ultra-clean workbench, high-pressure sterilization pot, gas bath constant temperature shaking incubator.

Preparation of Bacterial Suspension:

The experimental strains were inoculated in non-selective medium and placed in air at 37° C. for 24 h. Picking a single colony that grows well and inoculating it into broth medium, incubating at 35° C.±2° C. for 6 hours, and using LA broth medium to calibrate the concentration of the bacterial solution to 0.5 Mie turbidimetric tube ($1.5 \times 10^8$ CFU/mL). A bacterial suspension was obtained.

Paper Diffusion Drug Sensitivity Test:

Weighing the LB dry powder, sterilizing at 103.4 Kpa, 121.3° C. high-pressure steam for 15 min, and then putting it in a 40° C.-50° C. water bath. Placing a sterile empty plate (inner diameter 9 cm) on the surface of the ultra-clean table water table, shaking the LB, and then pouring the plate. The thickness of each plate was 3 mm to 4 mm. After the plate was cooled at room temperature, storing it in the refrigerator at 2° C.-8° C. Using a sterile cotton swab to dip the bacterial solution, and evenly coating the surface of the LB plate 3 times. After inoculation of the bacterial suspension, the LB plate was dried at room temperature for 3 min to 5 min. Using sterile forceps to closely attach the antibacterial drug paper to the dish. Putting the dish upside down and placing it in a 37° C. incubator for 24 h. Observing the result and measuring the diameter. Taking 0.5% DMSO solution as a negative control, the antibacterial activity was expressed by the diameter of the inhibition zone. The inhibition zone 17 mm, sensitive; the inhibition zone is 15 mm-16 mm, intermediary; the inhibition zone 14 mm, drug resistance.

Figure 2:
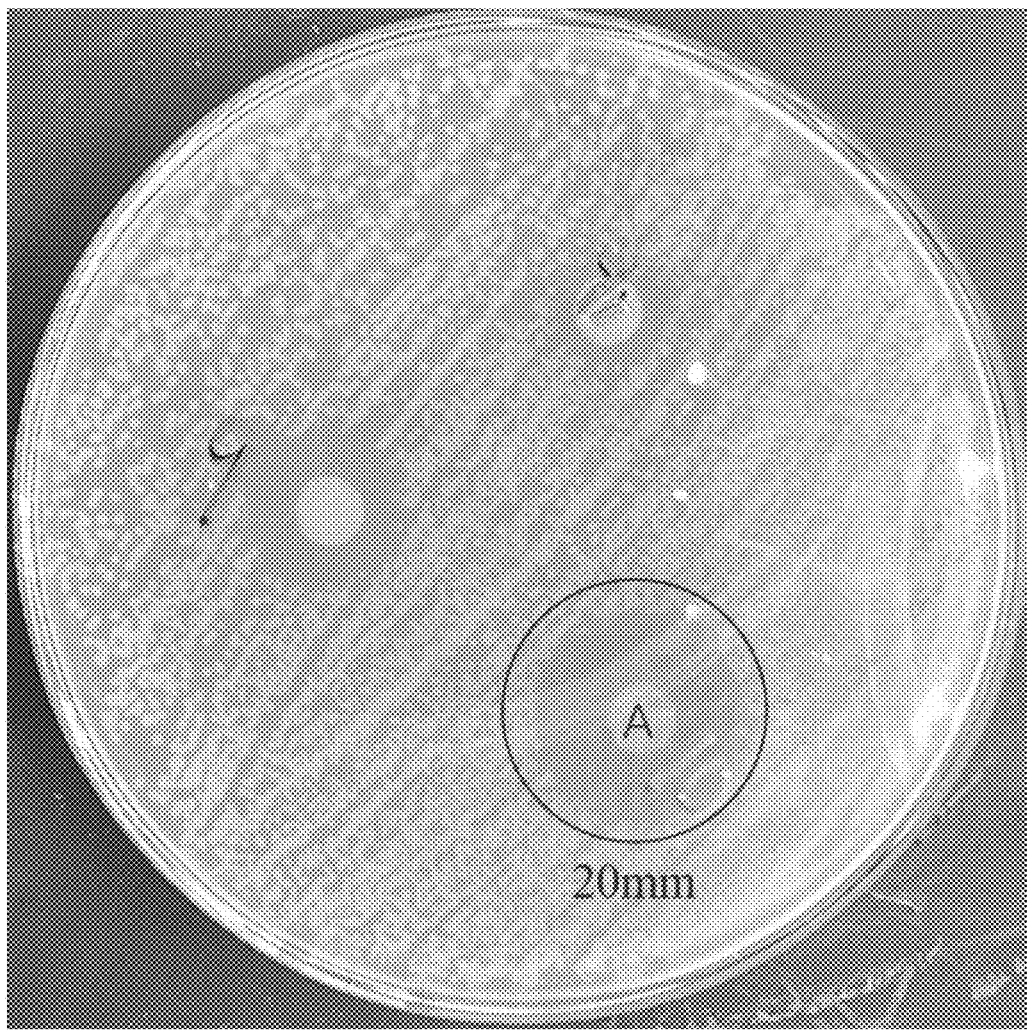
FIG. 2 shows the antibacterial effect of cinnamyl alcohol retinoic acid ester on multi-resistant *Staphylococcus aureus* 18-596.
Figure 3:
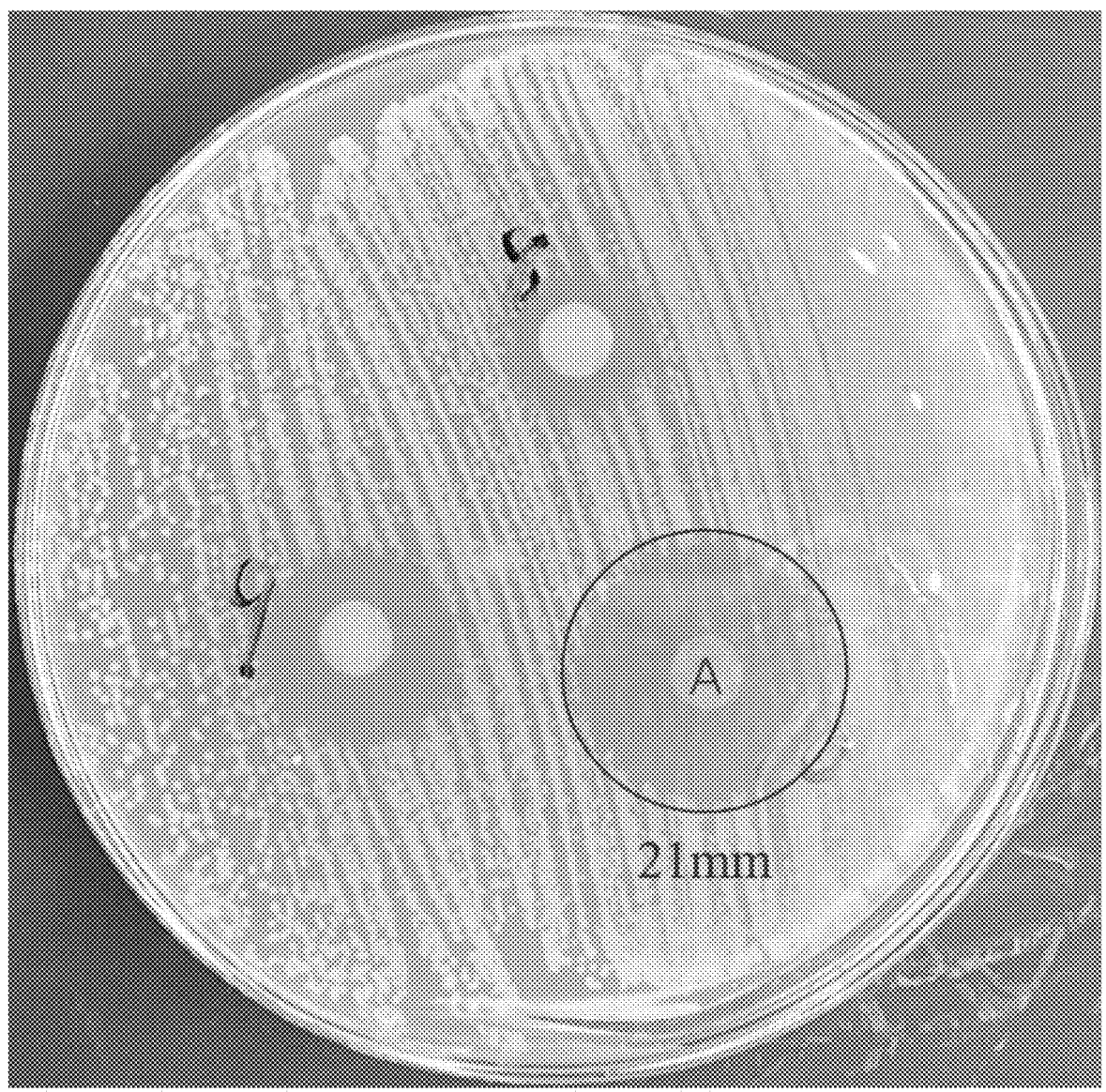
FIG. 3 shows the antibacterial effect of cinnamyl alcohol retinoic acid ester on multi-resistant *Pseudomonas aeruginosa* 18-202.

In FIGS. 2-3, cinnamyl alcohol retinoic acid ester was represented by A. FIG. 2 shows the antibacterial effect of cinnamyl alcohol retinoic acid ester on *Staphylococcus aureus* 18-596. FIG. 3 shows the antibacterial effect of cinnamyl alcohol retinoic acid ester on multi-resistant *Staphylococcus aureus* 18-596. The results are shown in Table 4.

TABLE 4

Experimental results of the zone of inhibition

| | Zone of inhibition/mm Strain | |
|---|---|---|
| Compound | Multi-resistant *Staphylococcus aureus* 18-596 | Multi-resistant *Pseudomonas aeruginosa* 18-202 |
| 0.5% DMSO | 0 | 0 |
| Gentamicin | 10 | 21 |
| Vancomycin | 21 | 9 |
| Retinoic acid | 8 | 7 |
| Cinnamyl alcohol | 14 | 6 |
| Cinnamyl alcohol retinoic acid ester | 20 | 21 |

The results in the following figure and Table 4 show that the raw materials cinnamyl alcohol and retinoic acid have little inhibitory effect on drug-resistant bacteria, but the cinnamyl alcohol retinoic acid shows strong resistance to multi-resistant *Staphylococcus aureus* 18-596 and multi-resistant *Pseudomonas aeruginosa* 18-202. In summary, the cinnamyl alcohol retinoic acid ester of the present invention can be used as an antibacterial drug candidate for multi-drug resistant bacteria, and further pre-clinical research is conducted. At the same time, the cinnamyl alcohol retinoic acid ester has excellent antioxidant activity, which further broadens its future production and sales roads.

What is claimed is:
1. A method comprising:
   reacting a compound of formula (II) with a compound of formula (III) to obtain a compound of formula (I):

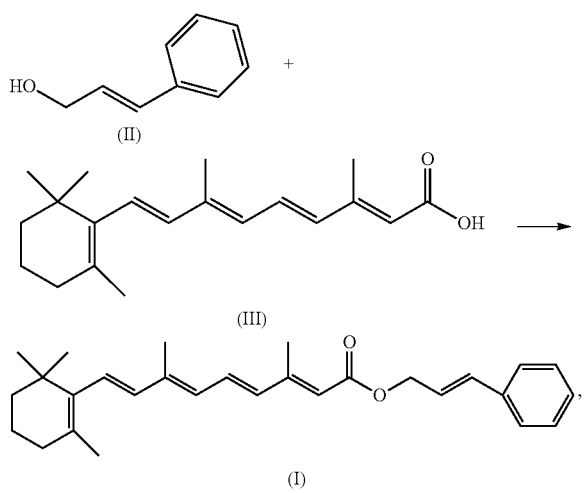

preparing a composition that includes the compound of formula (I), and
applying the composition as an antioxidant agent.

2. The method of claim 1, further comprising:
applying the composition as an antibacterial agent to inhibit *Staphylococcus aureus* 18-596 and *Staphylococcus aureus* 18-596.

3. The method of claim 1, wherein the reaction of the compound of formula (II) with the compound of formula (III) comprises the following steps:
placing the compound of formula (II) and the compound of formula (III), in a molar ratio of 1:1 to 1:1.3, in a reactor;
adding an organic solvent and a catalytic amount of 1-ethyl-3-(3 dimethylaminopropyl)carbodiimide under nitrogen atmosphere to obtain a reaction mixture; and
heating the reaction mixture at 60-90° C. for 4-8 hours; and
purifying the crude product on a silica gel fresh chromatography column with petroleum ether and ethyl acetate as an eluent to obtain the compound of formula (I).

4. The method of claim 3, wherein the organic solvent is toluene, tetrahydrofuran or acetonitrile.

5. The method of claim 3, wherein the organic solvent is toluene.

6. The method of claim 3, wherein the molar ratio of the compound of formula (II) and the compound of formula (III) is 1:1.1.

7. The method of claim 3, wherein the reaction mixture is heated at 80° C.

8. The method of claim 3, wherein the reaction mixture is heated for 7 hours.

9. The method of claim 3, wherein the eluent is petroleum ether:ethyl acetate=1:3.

10. The method of claim 1, wherein the reaction of the compound of formula (II) with the compound of formula (III) comprises the following steps:
placing the compound of formula (II), a catalyst, and an ionic liquid in a reactor under nitrogen atmosphere, the catalyst being 12-molybdosilicic acid hydrate ($H_6Mo_{12}O_{41}Si$);
adding the compound of formula (III) to the reactor to form a reaction mixture;
heating the reaction mixture at 20-50° C. for 5-10 hours;
placing the reaction mixture in a separating funnel to separate a crude product;
purifying the crude product by recrystallization in methanol to obtain the compound of formula (I); and
recycling the ionic liquid.

11. The method of claim 10, wherein the ionic liquid is 1-methyl-3-n-octylimidazolium tetrafluoroborate, 1-methyl-3-n-octylimidazolium hexafluorophosphate, or 1-butyl-3-methylimidazolium tetrafluoroborate ([BMIM][BF4]).

12. The method of claim 11, wherein the ionic liquid is 1-butyl-3-methylimidazolium tetrafluoroborate ([BMIM][BF4]).

13. The method of claim 10, wherein the compound of formula (II) and the compound (III) have a molar ratio of 1:1 to 1:1.3.

14. The method of claim 13, wherein the molar ratio of the compound of formula (II) and the compound of formula (III) is 1:1.1.

15. The method of claim 10, wherein the reaction mixture is heated at 20° C.

16. The method of claim 10, wherein the reaction mixture is heated for 8 hours.

* * * * *